United States Patent
Byerly

(10) Patent No.: US 9,981,088 B2
(45) Date of Patent: May 29, 2018

(54) PLUNGER FOR A MEDICATION CARTRIDGE

(71) Applicant: Eli Lilly and Company, Indianapolis, IN (US)

(72) Inventor: Roy Howard Byerly, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days. days.

(21) Appl. No.: 14/384,711

(22) PCT Filed: Mar. 18, 2013

(86) PCT No.: PCT/US2013/032783
§ 371 (c)(1),
(2) Date: Sep. 12, 2014

(87) PCT Pub. No.: WO2013/148394
PCT Pub. Date: Oct. 3, 2013

(65) Prior Publication Data
US 2015/0045741 A1    Feb. 12, 2015

Related U.S. Application Data

(60) Provisional application No. 61/616,123, filed on Mar. 27, 2012.

(51) Int. Cl.
A61M 5/315    (2006.01)
(52) U.S. Cl.
CPC .... *A61M 5/31513* (2013.01); *A61M 5/31515* (2013.01)
(58) Field of Classification Search
CPC ........................ A61M 5/31511; A61M 5/5066; A61M 5/315; A61M 5/31513; A61M 5/31515
See application file for complete search history.

(56) References Cited

U.S. PATENT DOCUMENTS 3,306,291 A    2/1967  Burke
5,094,148 A *  3/1992  Haber ............... A61M 5/31515
                                                        403/348
(Continued)

FOREIGN PATENT DOCUMENTS

WO    2002007812        1/2002
WO    2007/015469 A1    2/2007
(Continued)

OTHER PUBLICATIONS

Office Action issued by the Japanese Patent Office in Japanese Patent Application No. 2015-503362; dated Jan. 31, 2017; pp. 1-5 (English translation pp. 6-10); published in Japan.
(Continued)

*Primary Examiner* — Bradley J Osinski
(74) *Attorney, Agent, or Firm* — Jonathan Anderson

(57) ABSTRACT

A medication cartridge plunger including a sealing member, which is formed of a resilient material, and a force distributing member, which is attached to sealing member and formed of a material more rigid than the resilient material. The force distributing member is shaped complementary with the sealing member to distribute to the sealing member a medication expelling force that may be applied to the force distributing member by an external drive element to drive the plunger forward. The force distributing member includes a radial periphery fit within a hollow of the sealing member. The radial periphery has a plurality of apex regions connected by spanning regions, which apex regions are disposed along a common circle centered on an axial center of the medication cartridge plunger. The spanning regions are disposed within the common circle, and each apex region, relative to the common circle, is not in diametric alignment with any of the other apex regions.

14 Claims, 4 Drawing Sheets

(56) References Cited

U.S. PATENT DOCUMENTS

| | | |
|---|---|---|
| 5,688,252 A | 11/1997 | Matsuda et al. |
| 6,817,990 B2 | 11/2004 | Yap et al. |
| 7,666,169 B2 | 2/2010 | Cowan et al. |
| 2002/0022807 A1 | 2/2002 | Duchon et al. |
| 2003/0120219 A1 | 6/2003 | Nielsen et al. |
| 2007/0219508 A1 | 9/2007 | Bisegna et al. |
| 2011/0178475 A1 | 7/2011 | Tanaka et al. |

FOREIGN PATENT DOCUMENTS

| | | |
|---|---|---|
| WO | 2007118908 | 10/2007 |
| WO | 2009036496 | 3/2009 |

OTHER PUBLICATIONS

Patent Cooperation Treaty International Search Report and Written Opinion dated May 28, 2013 for International Application No. PCT/US2013/032783.

* cited by examiner

PLUNGER FOR A MEDICATION CARTRIDGE

BACKGROUND OF THE INVENTION

The present invention pertains to medication cartridges, and, in particular, to a plunger for a medication cartridge.

Many types of medication are provided in a cartridge including a plunger or piston that is slidable within a barrel of the cartridge. Movement of the plunger within the barrel can force medication from an outlet of the cartridge, such as a needle pierced septum at the cartridge forward end. Such plungers frequently are made of a resilient material with a radial periphery sized and shaped to provide a suitable fluid-tight seal with the interior of the cartridge barrel.

One problem with some resilient plungers is their susceptibility to local compression when acted upon by a drive member that extends into the cartridge barrel to contact and drive forward that plunger to expel the cartridge's medication contents. This compression may adversely impact the suitability of a plunger for certain uses, such as where a larger diameter plunger is needed but the accurate administration of small doses is still required.

To try and address this local compression, variously designed rigid elements have been incorporated into some resilient plungers. The rigid element is usually directly acted upon by the drive member and is sized and shaped to distribute applied load over a larger surface area of the resilient plunger. While useful to distribute loading, using a rigid element is not without its shortcomings.

For instance, a rigid element may force the resilient plunger during use to contact the cartridge barrel in places other than where a fluid tight seal is desired. Such contact results in a frictional resistance to motion of the plunger within the barrel that may, for example, adversely affect the glide force necessary to force movement of the plunger. However, shrinking the diameter of the rigid element, all the other things being equal, can decrease the surface area through which the force is transmitted to the resilient plunger portion, thereby decreasing its force distributing effectiveness. Furthermore, placing a rigid element on the rear end face of a resilient plunger such that it does not extend in a hollow of that plunger, and is less likely to squeeze along the rigid element radial periphery a portion of the resilient plunger against the barrel interior, makes the plunger assembly longer than may be desired.

Thus, it would be desirable to provide a medication cartridge plunger that reduces the chances for an undesired point of sealing contact with the cartridge barrel and to potentially overcome other shortcomings of the prior art.

BRIEF SUMMARY OF THE INVENTION

In one form thereof, the present invention provides a medication cartridge plunger including a sealing member and a force distributing member. The sealing member is formed of a resilient material and includes a body with a forward end, a rearward end, and a length that extends in an axial direction between the forward and rearward ends. Along the body length the sealing member includes at least one sealing surface extending around the body for a slideable, fluid-tight sealing engagement with an interior surface of a cartridge barrel in which the medication cartridge plunger is installed for use. A central region of the rearward end of the body includes a recessed surfaced that defines a hollow. The force distributing member is attached to the sealing member and formed of a material more rigid than the resilient material. The force distributing member is shaped complementary with the sealing member to distribute to the recessed surface a medication expelling force that may be applied to the force distributing member by an external drive element to drive the plunger forward. The force distributing member includes a radial periphery arranged transverse to the axial direction and fit within the body hollow. The radial periphery has a plurality of apex regions connected by spanning regions. The apex regions are disposed along a common circle and the spanning regions are disposed within the common circle. Each apex region, relative to the common circle, is not in diametric alignment with any of the other apex regions.

One advantage of the present invention is that a multiple piece plunger may be provided having a force-distributing back plate within a hollow provided in the back of a cartridge plunger sealing member and which back plate is configured to reduce the likelihood of undesired contact between the sealing member and the cartridge barrel in which such plunger slidably fits.

BRIEF DESCRIPTION OF THE DRAWINGS

The above-mentioned and other advantages and objects of this invention, and the manner of attaining them, will become more apparent, and the invention itself will be better understood, by reference to the following description of embodiments of the invention taken in conjunction with the accompanying drawings, wherein.

Figure 1:
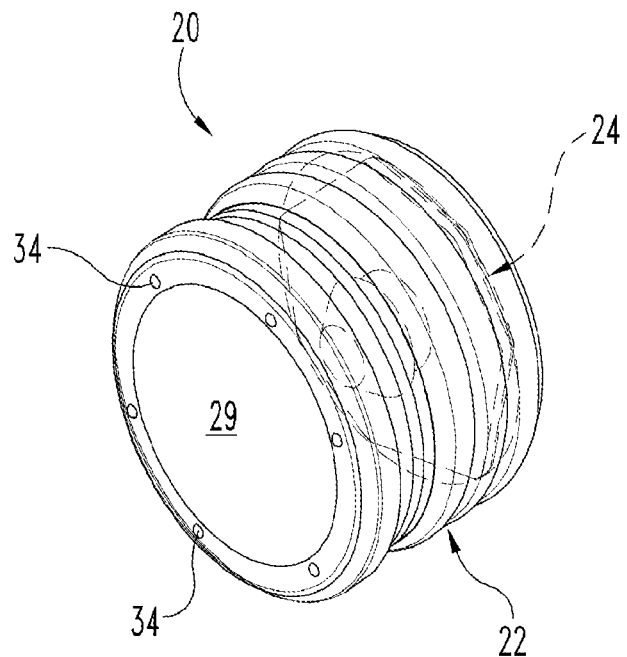
FIG. 1 is a front perspective view of a first embodiment of a cartridge plunger of the present invention.
Figure 2:
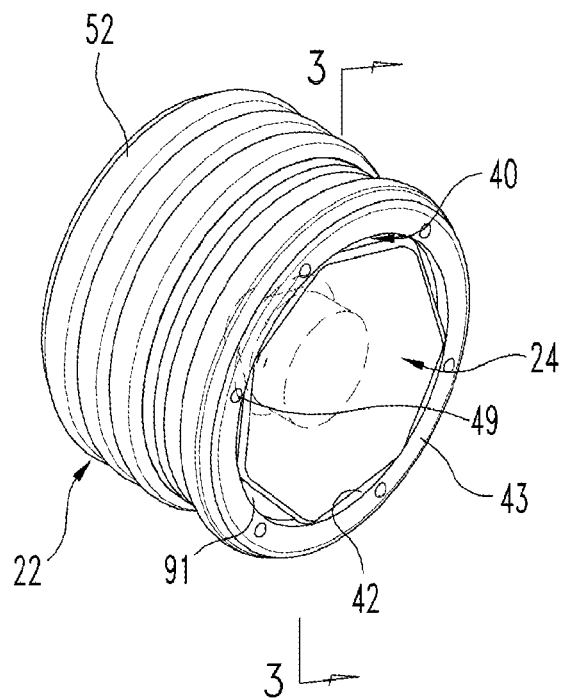
FIG. 2 is a rear perspective view of the cartridge plunger of FIG. 1.
Figure 3:
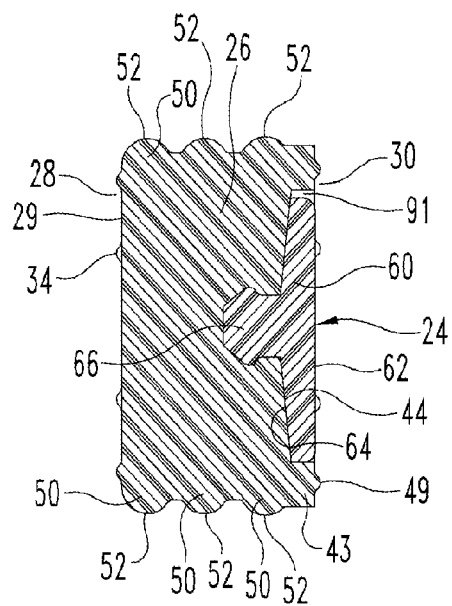
FIG. 3 is a cross-sectional side view, taken along line 3-3 of the cartridge plunger of FIG. 2.

Corresponding reference characters indicate corresponding parts throughout the several views. Although the drawings represent an embodiment of the present invention, the drawings are not necessarily to scale, and certain features may be exaggerated or omitted in some of the drawings in order to better illustrate and explain the present invention.

DETAILED DESCRIPTION OF THE INVENTION

Referring now to FIG. 1, there is shown a first embodiment of a medication cartridge plunger of the present invention. The medication cartridge plunger, generally designated 20, is assembled from two pieces. A first piece or sealing member, generally designated 22, provides suitable sealing characteristics relative to a cartridge barrel. A second piece or back plate, generally designated 24, serves to distribute to the sealing member force applied to the back plate by an external drive member.

Figure 8:
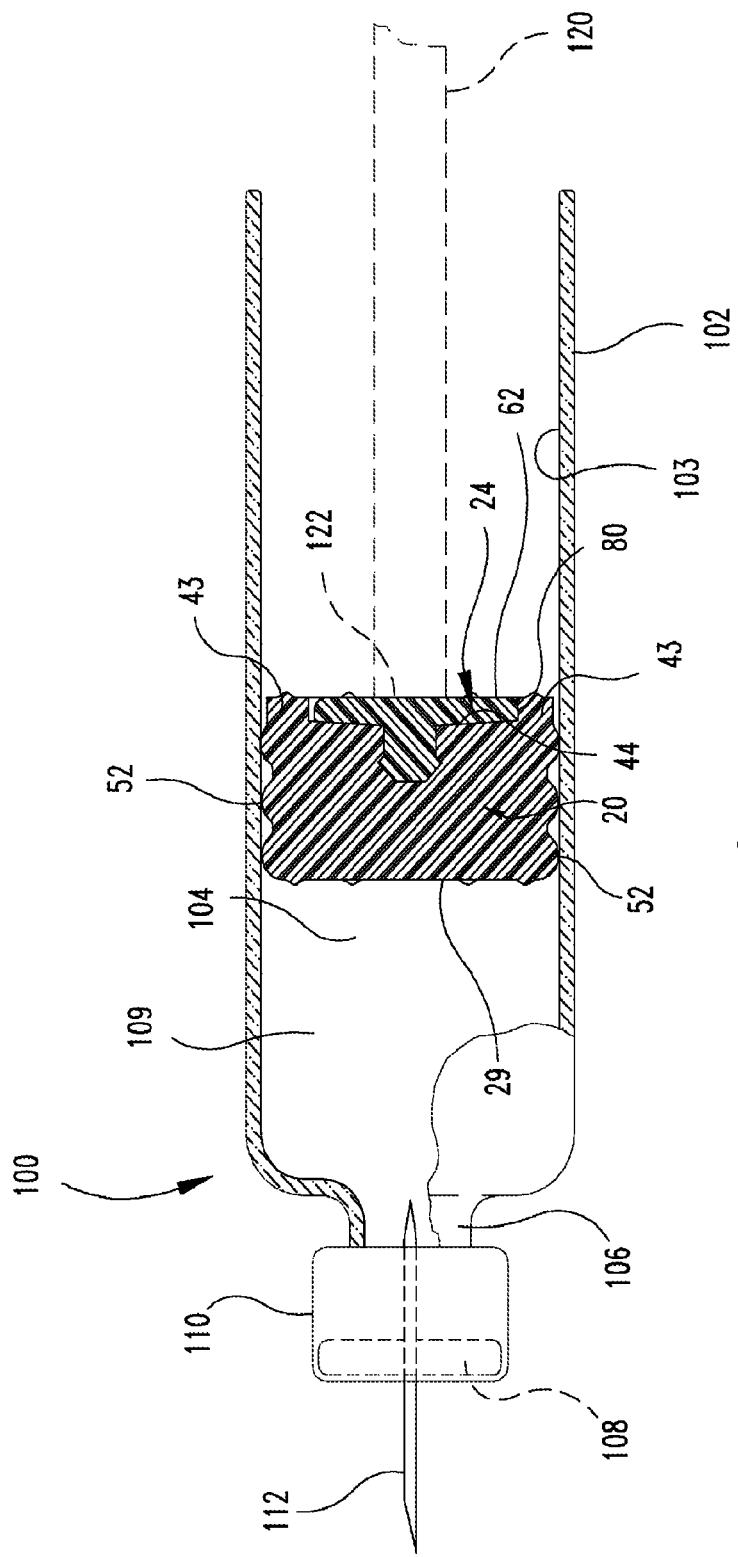
FIG. 8 is a side view, in partial cross section, of the cartridge plunger of FIGS. 1-7 within a cartridge, and wherein a drive member that is used to operatively engage and drive forward the cartridge plunger is also abstractly shown in dashed lines.

Sealing member 22 is formed in the shown embodiment from a single piece of resilient or elastomeric material. One suitable material is bromobutyl rubber available from Datwyler as FM257. Sealing member 22 comprises a body 26 having a forward end 28 and a rearward end 30 that are each oriented transverse to the axial direction in which the length of the body 26 extends between such ends. The face 29 of forward end 28 is flat but for a series of forwardly projecting nubs 34 that aid in preventing multiple plungers, during the manufacturing process, from sticking together. The reference to forward relates to a directional naming convention in which during dose dispensing the plunger is considered to move forward within a cartridge barrel. Forward end face 29 in use is in direct contact with the medication contents of a medication cartridge as shown in FIG. 8.

Figure 4:
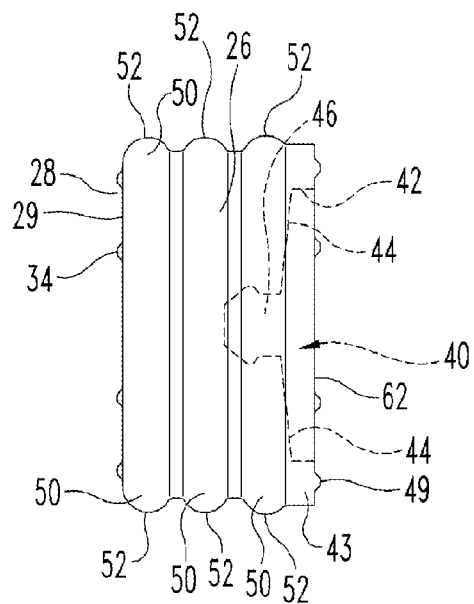
FIG. 4 is a side view of a sealing member shown separate from the other portion of the cartridge plunger of FIG. 1.
Figure 5:
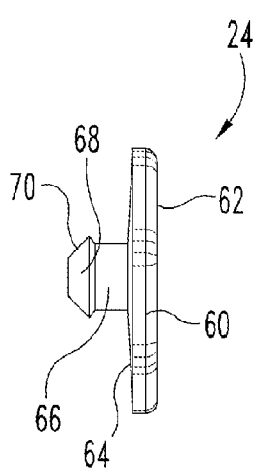
FIG. 5 is a side view of a back plate shown separate from the other portion of the cartridge plunger of FIG. 1.
Figure 6:
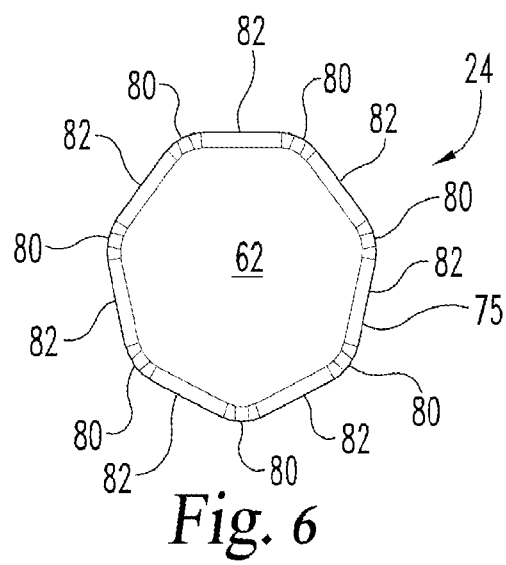
FIG. 6 is a rear end view of the back plate of FIG. 5.

The central region of rearward end 30 is recessed to define a hollow or cavity 40 for accommodating back plate 24. Hollow 40 is centered on and symmetric to the axis of body 26. As shown in FIG. 4, the hollow 40 is defined by a cylindrical surface 42 that is axially oriented and a disc-shaped surface 44 that slopes inward from surface 42 at a small angle, such as about eight degrees, from transverse to the axial direction.

As the plunger embodiment shown attaches the back plate to the sealing member with a frictional detent fit, the center portion of hollow surface 44 is further formed with a cavity 46 that is complementary to the attachment plug portion 66 of back plate 24. The hollow 40 could naturally be formed differently if, for example, the back plate were attached differently in an alternate embodiment, such a with a thread connection. Still further, if an adhesive were for used attachment instead of an interconnecting fit, the cavity 46 could be modified or eliminated entirely.

Cylindrical surface 42 is the radial inward face of a lip portion 43 of sealing member body 26. While lip portion 43 is designed to be symmetrical such that lip portion 43 has the same radial thickness at each point of its circumference, the manufacturing process can result in variances in such radial thickness. In one manufacturing process, multiple sealing members 22 are molded to be projecting from and integrally formed with a single sheet of the mold material, which sheet effectively extends from lip portion 43. The sealing members 22 are separated from the single sheet by punches that are intended to be axially aligned with the sealing members, but in practice may be slightly offset therefrom, which offsetting realizes a lip 43 of the individual sealing member 22 that is not symmetrical with the sealing member axis. Nubs 49 on the rear of lip portion 43 prevent sticking during manufacture.

Body 26 between ends 28 and 30 has a generally cylindrical periphery other than for a plurality of radially projecting sealing ribs 50. Each sealing rib 50 extends around the entire circumference of body 26 and is oriented transverse to the axial direction. Each rib 50 includes a radiused sealing surface 52 at its outer radial extent. As is conventional, ribs 50 are sized and shaped such that sealing surfaces 52 press against, in slideable fluid-tight sealing engagement with, an interior surface of a cartridge barrel in which the medication cartridge plunger is installed for use.

The sealing ribs 50 with their surfaces 52 are shown as three in number and in axially spaced relationship along the body length, resulting in three different sealing rings for the plunger. The number of ribs 50 and resulting surfaces 52 may be selected by one of skill in the art to provide suitable sealing characteristics in view of the overall design of the plunger. As a result, different numbers of such ribs, such as two, or as few as one, or more than three, can be provided in alternate embodiments.

Back plate 24 is molded as a single piece out of a material more rigid than the material of sealing member 22 One suitable material is polycarbonate with 30% glass fiber available from Sabic Innovative Plastics as LNP Thermocomp DF006ER. Back plate 24 includes a plate portion 60 having a rearward face 62 and a forward face 64. An attachment plug portion 66 of back plate 24 projects forward from the central region of forward face 64. Rearward face 62, which is oriented transverse to the axial direction, is the surface that an external drive member may apply a force to so as to drive plunger 20 forward within the medication cartridge barrel during use to expel medication. Forward face 64, which is shaped complementary to the angling of sealing member surface 44 to be pressed thereagainst during plunger driving, is the surface which distributes to the sealing member 22 the expelling force applied to the plate face 62.

Plug portion 66 includes an enlarged head 68 with a beveled tip 70. Plug portion 66 can be force fit during manufacturing assembly into complementary cavity 46 to attach back plate 24 to sealing member 22.

Plate portion 60 of back plate 24 is sized to fit within hollow 40 so as to be axially centered on sealing member 22. In the shown embodiment, rearward face 62 is coplanar with body rearward end 30. In alternate embodiments, back plate 24 could fit within hollow 40 with rearward face 62 being recessed from or projecting beyond end 30.

Plate portion 60 includes a radial periphery 75 arranged transverse to the axial direction and which is polygonal in shape. The shown polygonal shape has an odd number of sides and is equilateral. The radial periphery is formed by seven curved apex regions 80 in series with seven spanning regions 82.

Figure 7:
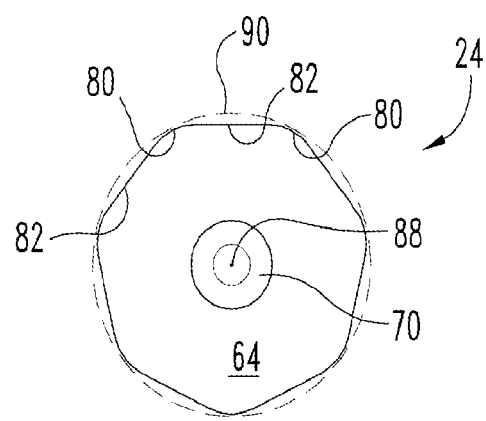
FIG. 7 is a front view of the back plate of FIG. 5, and wherein the circle on which the radial outer tips of the back plate lie is shown in dashed lines.

The radial periphery 75 is inscribed in a circle in that each apex region 80 has a radial reach disposed along a common circle centered on an axial center indicated at 88. When back plate 24 is assembled to sealing member 22, center 88 lies on the axis of the plunger, and the common circle, which is shown in dashed lines at 90 in FIG. 7, is aligned with and approximately the same size as the circle defined by cylindrical surface 42 as such surface 42 is configured when member 26 is slightly deformed when inserted into a syringe barrel. No apex region 80, relative to common circle 90, is in diametric alignment with any of the other apex regions 80 due to the polygonal shape being equilateral and formed with an odd number of sides.

Each spanning region 82 connects two angularly adjacent apex regions 80 and is disposed within common circle 90. Each apex region 80 is formed as a radiused curve, with the point of tangency of the apex region 80 with circle 90 being centered on the length of the curve. The spanning regions 82 are straight along their lengths and form a majority, such as about seventy-five percent, of the actual length of the plate radial periphery. The straight shape and connecting length of spanning regions 82 results in them forming straight segments of the back plate radial periphery which are arranged chord-like relative to common circle 90.

In alternate embodiments of the back plate, fewer, such as five, or more, apex regions may be employed, but in any case odd number of such regions is preferred over an even number. Such preference is a result of the fact that both a non-diametric alignment of the apex regions and an equilateral polygonal shape is preferred. Providing a back plate with an even number of apex regions is possible, but providing non-diametric alignment of the apex regions for such a design requires a non-equilateral polygonal shape. Still further, and rather than radiused curves, the apex regions alternatively could merely be points of intersection of the spanning segments 82.

Plunger 20 and its benefits will be understood still further in view of the following description of its operation. Plunger 20 is shown in FIG. 8 as part of a medication cartridge, generally designated 100, that is otherwise of conventional design. Plunger 20 is shown being acted upon by a drive member 120. Plunger 20 can be used in cartridges of less conventional design as well.

Cartridge 100 can be installed in a variety of known devices, such as an injection pen or otherwise shaped injection device. Medication cartridge 100 includes a barrel 102, such as made of a molded plastic material. Barrel 102 includes a cylindrical interior surface 103 that the sealing surfaces 52 of plunger 20 engage in a fluid-tight manner. The interior hollow 104 of barrel 102 forward of plunger forward face 29 is filled with medication 109 for dispensing. The opening in the forward neck 106 of barrel 102 is capped by a septum 108 secured by a crimp seal 110. A double ended needle abstractly shown at 112 pierces septum 108 to provide an outlet by which medication 109 can be expelled when plunger 20 is driven forward, or to the left in the FIG. 8 embodiment. Needle 112 is often associated with a needle assembly that can be removable mounted to, for example, the injection pen with which cartridge 10 is installed for use.

Plunger 20 is slidably driven forward within barrel 102 by the drive member abstractly shown at 120 that is part of the injection device in which the cartridge 100 is installed for use. As drive member 120 is advanced to the left in FIG. 8 further into the barrel interior, the drive member lead end 122 pushes against back plate rear surface 62 to advance plunger 20 forward.

The back plate 24, as its surface area contacting the sealing member is a larger area than the area of lead end 122, distributes the load over a larger area of plunger sealing member surface 44. The large radial extent of back plate 24 results in force being applied to the sealing member 26 close to the inner diameter of the cartridge barrel so as to reduce elastomeric effects. The space between spanning segments 82 and circle 90 provides room for non-symmetrical larger portions of lip 43 to deform into, which results in the lip 43 being less likely to be squeezed against the barrel interior by the rigid plate 24 in a manner that results in an undesired large frictional resistance to plunger movements. As a result of the back plate design, large radial dimensions can be provided to the back plate periphery while reducing the likelihood of undesired drag While this invention has been shown and described as having preferred designs, the present invention may be modified within the spirit and scope of this disclosure. For example, the plunger sealing member can be formed of more than a single piece, such as a central portion with one or more separate O-rings secured therearound, but the back plate of the present invention is well suited for one piece resilient members. This application is therefore intended to cover any variations, uses or adaptations of the invention using its general principles. Further, this application is intended to cover such departures from the present disclosure as come within known or customary practice in the art to which this invention pertains.

I claim:

1. A medication cartridge plunger comprising:
    a sealing member formed of a resilient material, said sealing member including a body with a forward end, a rearward end, and a length that extends in an axial direction between said forward end and said rearward end, wherein along said body length said sealing member includes at least one sealing surface extending around said body for a slideable, fluid-tight sealing engagement with an interior surface of a cartridge barrel in which the medication cartridge plunger is installed for use, wherein a central region of said rearward end of said body includes a recessed surface that defines a plate portion accommodating hollow and an attachment portion receiving cavity; and
    a force distributing member including a plate portion and an attachment portion projecting forward from said plate portion, said plate portion attached to said sealing member by said attachment portion fitting within said attachment portion receiving cavity, said force distributing member formed of a material more rigid than said resilient material, said plate portion shaped complementary with said sealing member to distribute to said recessed surface a medication expelling force that may be applied to said plate portion by an external drive element to drive the plunger forward, wherein a forward face of the plate portion contacts the recessed surface of the sealing member to distribute the medication expelling force to said recessed surface, said plate portion including an outer radial periphery arranged transverse to the axial direction and fit within said plate portion accommodating hollow, said outer radial periphery having a plurality of apex regions connected by spanning regions, said apex regions disposed along a common circle, said spanning regions disposed within said common circle, wherein each said apex region, relative to the common circle, is not in diametric alignment with any of the other apex regions.

2. The medication cartridge plunger of claim 1 wherein said spanning regions form a majority portion of a length of said outer radial periphery.

3. The medication cartridge plunger of claim 2 wherein said spanning regions form straight segments of said outer radial periphery which are arranged chord-like relative to the common circle.

4. The medication cartridge plunger of claim 1 wherein said plurality of apex regions consist of an odd number of apex regions.

5. The medication cartridge plunger of claim 1 wherein said common circle is centered on an axial center of the medication cartridge plunger.

6. The medication cartridge plunger of claim 1 wherein said plate portion has a rearward face coplanar with said body rearward end.

7. The medication cartridge plunger of claim 1 wherein the plate portion forms a rearward face of the medication cartridge plunger adapted to engage the external drive element.

8. The medication cartridge plunger of claim 1 wherein the attachment portion attaches to the sealing member with a frictional detent fit.

9. The medication cartridge plunger of claim 1 wherein the attachment portion includes an enlarged head configured to attach the plate portion to the sealing member.

10. The medication cartridge plunger of claim 1 wherein the attachment portion blocks relative axial movement of the force distributing member and the sealing member.

11. A medication cartridge including:
    a barrel including an outlet;
    a plunger positioned in the barrel; and a drive member positioned rearward of the plunger and configured to apply a driving force to the plunger to drive the plunger forward, wherein said plunger includes a sealing member formed of a resilient material, said sealing member including a body with a forward end, a rearward end, and a length that extends in an axial direction between said forward end and said rearward end, said sealing member including at least one sealing surface for a fluid-tight sealing engagement with an interior surface of the barrel, the rearward end of said sealing member including a recessed surface that defines a plate portion accommodating hollow and an attachment portion receiving cavity positioned forward of the plate portion accommodating hollow, and a force distributing member including a plate portion and an attachment portion projecting forward from said plate portion and attaching said force distributing member to the sealing member, said force distributing member formed of a material more rigid than said resilient material, said plate portion engaging said recessed surface of said sealing member to distribute to said recessed surface said driving force, said plate portion including an outer radial periphery arranged transverse to the axial direction and fit within said plate portion accommodating hollow, said outer radial periphery having a plurality of apex regions connected by spanning regions, said apex regions disposed along a common circle, said spanning regions disposed within said common circle, wherein each said apex region, relative to the common circle, is not in diametric alignment with any of the other apex regions.

12. The medication cartridge of claim 11 further including a medication positioned in the barrel between the plunger and the outlet, wherein said driving force is operative to expel the medication from the barrel through the outlet.

13. The medication cartridge of claim 11 wherein the drive member includes a lead end configured to engage a rearward face of the plate portion of the plunger, and a surface area of the plate portion contacting the sealing member is greater than a surface area of the lead end engaging the plate portion.

14. The medication cartridge of claim 11 wherein the attachment portion attaches to the sealing member with a frictional detent fit.

* * * * *